US011324587B2

(12) United States Patent
Balachandran

(10) Patent No.: US 11,324,587 B2
(45) Date of Patent: May 10, 2022

(54) CORNEAL IMPLANT

(71) Applicant: Chandrashekar Balachandran, Killara (AU)

(72) Inventor: Chandrashekar Balachandran, Killara (AU)

( * ) Notice: Subject to any disclaimer, the term of this patent is extended or adjusted under 35 U.S.C. 154(b) by 28 days.

(21) Appl. No.: 16/118,843

(22) Filed: Aug. 31, 2018

(65) Prior Publication Data

US 2019/0060054 A1 Feb. 28, 2019

(30) Foreign Application Priority Data

Aug. 31, 2017 (AU) ................. 2017903503

(51) Int. Cl.
*A61F 2/14* (2006.01)
*A61L 27/38* (2006.01)

(52) U.S. Cl.
CPC .............. *A61F 2/148* (2013.01); *A61F 2/142* (2013.01); *A61L 27/3808* (2013.01); *A61L 27/3839* (2013.01); *A61L 27/3886* (2013.01); *A61F 2230/0002* (2013.01); *A61F 2250/0053* (2013.01); *A61F 2250/0071* (2013.01); *A61F 2250/0097* (2013.01); *A61L 2430/16* (2013.01)

(58) Field of Classification Search
CPC .......... A61F 2/142; A61F 2/148; A61F 2/145; A61F 2/1453; A61F 2230/001; A61F 2250/0053; A61F 2250/0071; A61F 2250/0091; A61L 27/3808; A61L 27/3839; A61L 27/3886; A61L 2430/16
See application file for complete search history.

(56) References Cited

U.S. PATENT DOCUMENTS

| 5,139,518 | A | * | 8/1992 | White | A61F 2/142 128/898 |
| 6,789,544 | B2 | * | 9/2004 | Busin | A61F 2/142 128/898 |
| 9,724,234 | B2 | * | 8/2017 | Murphy | A61F 2/142 |
| 2007/0244559 | A1 | * | 10/2007 | Shiuey | A61F 9/007 623/5.11 |
| 2010/0211051 | A1 | * | 8/2010 | Weston | A61F 2/148 606/1 |
| 2011/0166650 | A1 | * | 7/2011 | Busin | A61F 2/142 623/5.11 |
| 2012/0009159 | A1 | * | 1/2012 | Humayun | A61K 35/545 424/93.7 |
| 2012/0059488 | A1 | | 3/2012 | Shimmura | |
| 2014/0155871 | A1 | * | 6/2014 | Cumming | A61F 2/142 606/5 |

(Continued)

FOREIGN PATENT DOCUMENTS

WO 2008155748 A2 12/2008
WO 2015111040 A1 7/2015

OTHER PUBLICATIONS

European Patent Office—Extended European Search Report—Application No. EP 18191927, dated Jan. 7, 2019, 7 pages.

*Primary Examiner* — Paul B Prebilic
(74) *Attorney, Agent, or Firm* — Sunstein LLP

(57) ABSTRACT

A corneal implant and methods of forming and implanting the implant are described. The corneal implant comprises a portion of corneal endothelial tissue and a portion of scleral tissue. The corneal implant is keyhole shaped, with a disc portion and a tail portion. The tail portion may further comprise a perforated section.

15 Claims, 8 Drawing Sheets

(56) References Cited

U.S. PATENT DOCUMENTS

2015/0223930 A1* 8/2015 Shiuey .................... A61F 2/142
                                                         623/5.14
2016/0331515 A1* 11/2016 Ben Nun ................ A61F 2/148

* cited by examiner

CORNEAL IMPLANT

CROSS-REFERENCE TO RELATED APPLICATIONS

This application claims priority from Australian Application No. 2017903503 filed Aug. 31, 2017, and entitled "Corneal Implant," which is hereby incorporated herein by reference in its entirety.

TECHNICAL FIELD

The present invention relates to a corneal implant and a method and apparatus for corneal transplantation.

BACKGROUND SECTION

The cornea is the front window of the eye. It consists of multiple layers. From superficial to deep they are the epithelium, stroma and endothelium. Each layer can be affected by different diseases. The corneal endothelium can be affected in diseases such as Fuchs' endothelial dystrophy and pseudophakic bullous keratopathy which result in the reduction on corneal endothelial cell density. The corneal endothelium consists of a monolayer of cells that do not replicate. Therefore, they can only be replaced by transplantation of cells from another person's cornea.

Transplantation techniques are evolving. They range from full thickness grafts (i.e. penetrating keratoplasty) to partial thickness grafts such as Descemet Stripping Endothelial Keraplasty (DSEK/DSAEK) to just the monolayer of corneal endothelium-Descemet's membrane complex called Descement Membrane Endotheial Keratoplasy (DMEK). The endothelium-descement graft complex is 10-15 microns thick. By replacing only that which is needed, smaller incisions can be made and less astigmatism can be induced such as with penetrating keratoplasty. The graft host interface is also kept clear of haze reducing risk of visual disturbance which may be seen with DSEK/DSAEK.

DMEK surgery involves a few challenges. Firstly, the graft needs to be harvested without touching the endothelium with instruments. Once harvested, the endothelium-descemet complex immediately rolls into either a single or a double scroll with the endothelium facing outwards. This scroll has to be inserted in the anterior chamber, centered and unrolled with the endothelium facing posteriorly. All these maneuvers have to be conducted without any instruments touching the graft. Instead, balanced salt solution &/or air injected through a cannula is used to manipulate the Descemet endothelial graft complex. Once unrolled and centered, air is injected deep to the graft to raise the graft to the posterior surface of the cornea. Air is left in the anterior chamber for an hour for the graft to adhere.

SUMMARY OF THE INVENTION

In a first aspect the invention provides a corneal implant comprising a portion of corneal endothelial tissue and a portion of scleral tissue.

Preferably the portion of endothelial tissue is disk shaped.
Preferably the portion of scleral tissue extends from the edge of the portion of endothelial tissue.
Preferably the portion of scleral tissue is tail shaped.
Preferably the corneal implant comprises a tail portion, the tail portion being sceleral tissue.
Preferably the portion of corneal endothelial tissue and the portion of scleral tissue are integral.
Preferably the corneal implant is keyhole shaped.
Preferably the corneal implant comprises a perforated section.
Preferably the perforated section is within the portion of scleral tissue.
Preferably the perforated section is positioned at a junction of the portions of the corneal endothelial tissue and the sclera tissue.
Preferably the thickness of the portion of corneal endothelial tissue is in the range of 10-15 µm.
Preferably the corneal implant is cut from a cornea.
Preferably the corneal implant is suitable for insertion into the anterior chamber of an eye and for adhering to the posterior surface of the cornea.
Preferably the implant comprises a disc shape and having a tail extending from the disk.
Preferably the portion of scleral tissue is comprised within the tail.
Preferably the portion of corneal endothelial tissue comprises corneal endothelium and Descement membrane.

In a second aspect the invention provides a method for preparation of a corneal implant comprising the steps of harvesting a corneal implant from the posterior surface of a cornea, the corneal implant comprising a portion of corneal endothelial tissue and a portion of scleral tissue.

Preferably the step of harvesting comprises the steps of applying a trephine to the posterior surface of the cornea to harvest the corneal implant.
Preferably the trephination is decentered on the posterior surface of the cornea.

In a third aspect the invention provides a corneal implant comprising an implant portion and a manipulating portion.

Preferably the implant portion comprises corneal endothelial tissue.
Preferably the manipulating portion comprises scleral tissue.
Preferably the corneal implant comprises a disc portion and a tail portion, wherein the tail portion comprises the manipulating portion.

In a fourth aspect the invention provides a method for performing a corneal transplantation comprising the steps of:
a. inserting at least part of a corneal implant into the anterior chamber of the eye, the corneal implant comprising an implant portion and a manipulating portion, the manipulating portion comprising non-endothelial tissue;
b. positioning the implant portion of the implant to adhere to the posterior surface of the cornea using the manipulating portion.

Preferably the implant portion comprises corneal endothelial tissue.
Preferably the implant portion is disc shaped.
Preferably the manipulating portion extends from the edge of the implant portion.
Preferably the manipulating portion is tail shaped.
Preferably the manipulating portion comprises scleral tissue.
Preferably the step of inserting comprises positioning the implant portion into the anterior chamber of the eye and retaining at least part of the manipulating portion outside of the eye.
Preferably the implant portion is scroll shaped during insertion.
Preferably the step of insertion comprises:
a. using a syringe to inject the corneal implant into the anterior chamber of the eye.

Preferably the corneal implant is inserted into the anterior chamber of the eye through an incision in the sclera.

Preferably a suture is placed in the manipulating portion.

Preferably the step of placing a suture in the manipulating portion closes the incision.

In a fifth aspect the invention provides a method for performing a corneal transplantation comprising the steps of:
a. inserting at least part of a corneal implant according to the first aspect and the third aspect into the anterior chamber of the eye;
b. positioning the implant portion of the implant to adhere to the posterior surface of the cornea.

In a sixth aspect the invention provides a kit comprising the corneal implant of any one the first aspect and the third aspect and a fluid.

Embodiments further comprise a delivery device for inserting the corneal implant into the anterior portion of an eye.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF THE DRAWINGS

Figure 1:
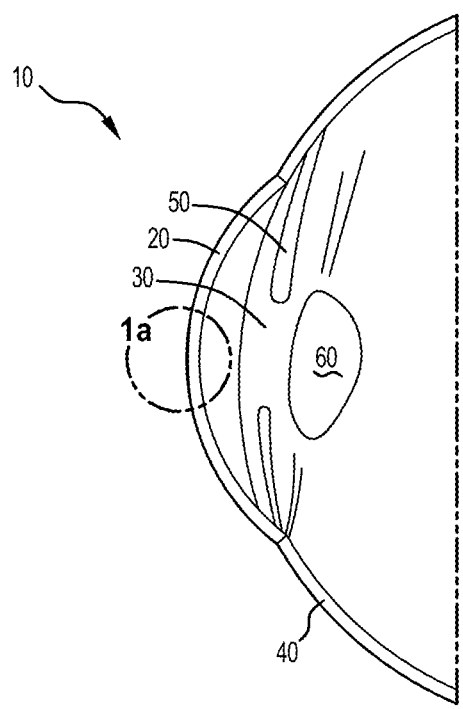
FIG. 1 is an illustration of the basic structure of a human eye.

FIG. 1 shows the basic structure of the eye. FIG. 1 is a cross-sectional representation of the front section of the eye. The cornea 20 is the transparent front part of the eye. The cornea is a circular section and surrounded on all sides by sclera 40. The sclera is the white of the eye. Behind the cornea is the anterior chamber 30. The iris 50 and lens 60 are positioned behind cornea 20.

Figure 1A:
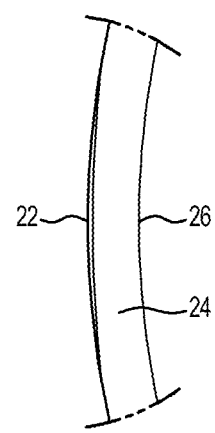
FIG. 1a is an exploded section of the cornea.

The cornea has multiple layers as shown in exploded view in FIG. 1a. The outer layer is the corneal epithelium 22. The thick transparent middle layer is the corneal stroma 24. The rear layer of the cornea is the corneal endothelium. The corneal endothelium is a single layer of cells having a typical thickness of between 5 to 15 microns. The cells of the corneal endothelium do not replicate. The corneal endothelium can be affected in diseases such as Fuchs' endothelial dystrophy which can result in the reduction of corneal endothelial cell density. Deterioration of the corneal endothelium can cause a gradual decline in vision and clouding.

We now describe a new treatment to replace corneal endothelium tissue using a corneal implant.

In the present invention replacement of corneal endothelium is performed by creating a corneal implant from a donor eye.

Figure 2:
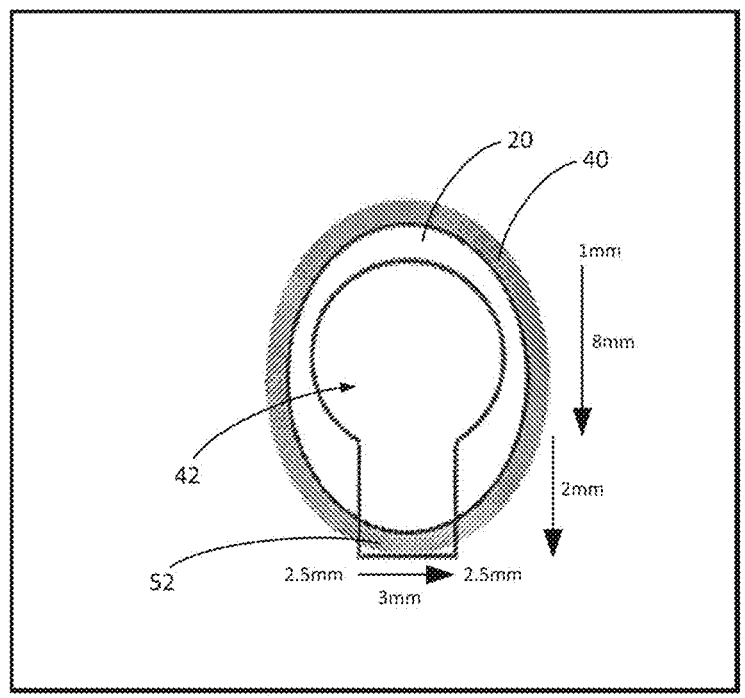
FIG. 2 shows the corneal implant within a donor cornea.

FIG. 2 shows a cornea 20 and surrounding portion of sclera 40. Typically this portion of the eye is removed from the donor eye and positioned with the endothelial tissue facing upward in trephine punch block. A keyhole shaped trephine (shown in FIGS. 4-6) is applied to the posterior side of the cornea covered with the layer of corneal endothelium to cut the corneal implant from the donor cornea. The resulting corneal implant after extraction from the cornea is shown in FIG. 3.

As illustrated in FIG. 2, the corneal implant includes a portion of corneal endothelial tissue 42 and a portion of sclera tissue 52. As shown in FIG. 2 the trephine is decentered with respect to the donor cornea in order to harvest a central disc with as long tail as possible.

Figure 3:
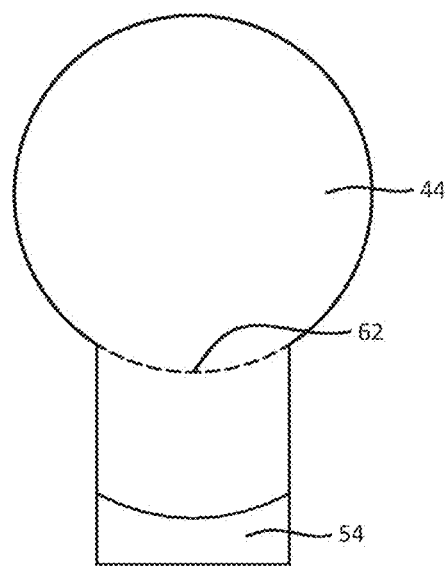
FIG. 3 illustrates a corneal implant.

As illustrated in FIGS. 2 and 3 the corneal implant is generally keyhole shaped. The keyhole includes a disc shaped portion 44. The implant includes a tail shaped extension 54 from the edge of the disc shaped portion.

In an embodiment of FIGS. 2 and 3 the portion of the corneal implant comprising sclera tissue 52 is only a small portion at the end of the tail section. In further embodiments the trephine may be arranged to allow a different percentage portion of the tail section to be cut from the sclera part of the eye and so the junction between the endothelia tissue and sclera tissue may be at a different position within the tail. In a further embodiment the tail may not include any scleral tissue. The implant is cut in a single portion and the disc and tail portions of the implant are integral.

Example dimensions for the implant are shown in FIG. 2. These dimensions are for illustrative purposes only and are not limiting. In particular the dimensions may be determined specifically for patient undergoing surgery depending on the size of the eye for surgery, the size of the donor eye and the size of the endothelial tissue requiring transplant. In the example of FIG. 2 the disc shaped portion of the implant has a diameter of around 8 mm. The tail portion has a length of around 2 mm and width of around 3 mm.

In a further embodiment the above non circular corneal implant shape could be generated using a laser to achieve the same design.

In some embodiments of the invention a perforated section 62 is incorporated into the implant. In the embodiment of FIG. 3, perforated section 62 is positioned at the junction between the disc shaped section of the corneal implant and the tail section. In further embodiments the perforated section may be positioned within the tail section of the implant. The perforated section is included in order that part of the tail section may be easily removed from the implant during surgery. This is discussed in more detail below with reference to FIGS. 7 and 8. In embodiments, the perforated section may be created using a needle or a laser. Typically, the perforated section includes a series of cuts through the implant in order to weaken the implant at that position. The perforations may be added after transplantation in to the use a small needle or a laser. The perforation is placed to remove the tail from the graft where necessary to do so. In the preferred embodiment, the perforation would be circumferential in position to allow the tail to be removed. In other embodiments a variable amount of the tail as preferred by the surgeon could be removed.

The preparation process of the implant involves a step of separating the endothelial layer from the stroma layer within the donor eye. This is performed by pealing the endothelial layer from the stroma layer. The graft is placed in a curved plastic well with vacuum generated using a syringe to hold the graft. Once secured the endothelium is separated by creating an incision close to the trabecular meshwork. It is then dissected forwards with blunt dissention breaking collagen attachments towards the center and separated from the underlying stroma. In one embodiment the endothelium is separated over the entire donor surface and then trephined. In another embodiment the endothelium is kept attached along a variable circumference of the sclera such as 2 mm so that the tail incorporates a section the sclera.

Further embodiments do not include perforations. In such embodiments the tail portion may be cut or torn away after transplantation.

In preferred embodiments all layers of the cornea are maintained during extraction of the corneal implant during trephination in order to maintain the integrity of the implant after the implant has been cut from the cornea the endothelia layer is peeled from the stroma layer. Once trephined the stroma is cut away from the descement endothelium complex near the tail. However, in further embodiments the endothelia layer may be separated from the stroma layer before the implant is cut from the donor eye. The corneal implant is then stained with methylene blue to help visualize the graft once it is inserted into the recipient eye.

Figure 4:
FIG. 4 is a side view of a trephine.
Figure 5:
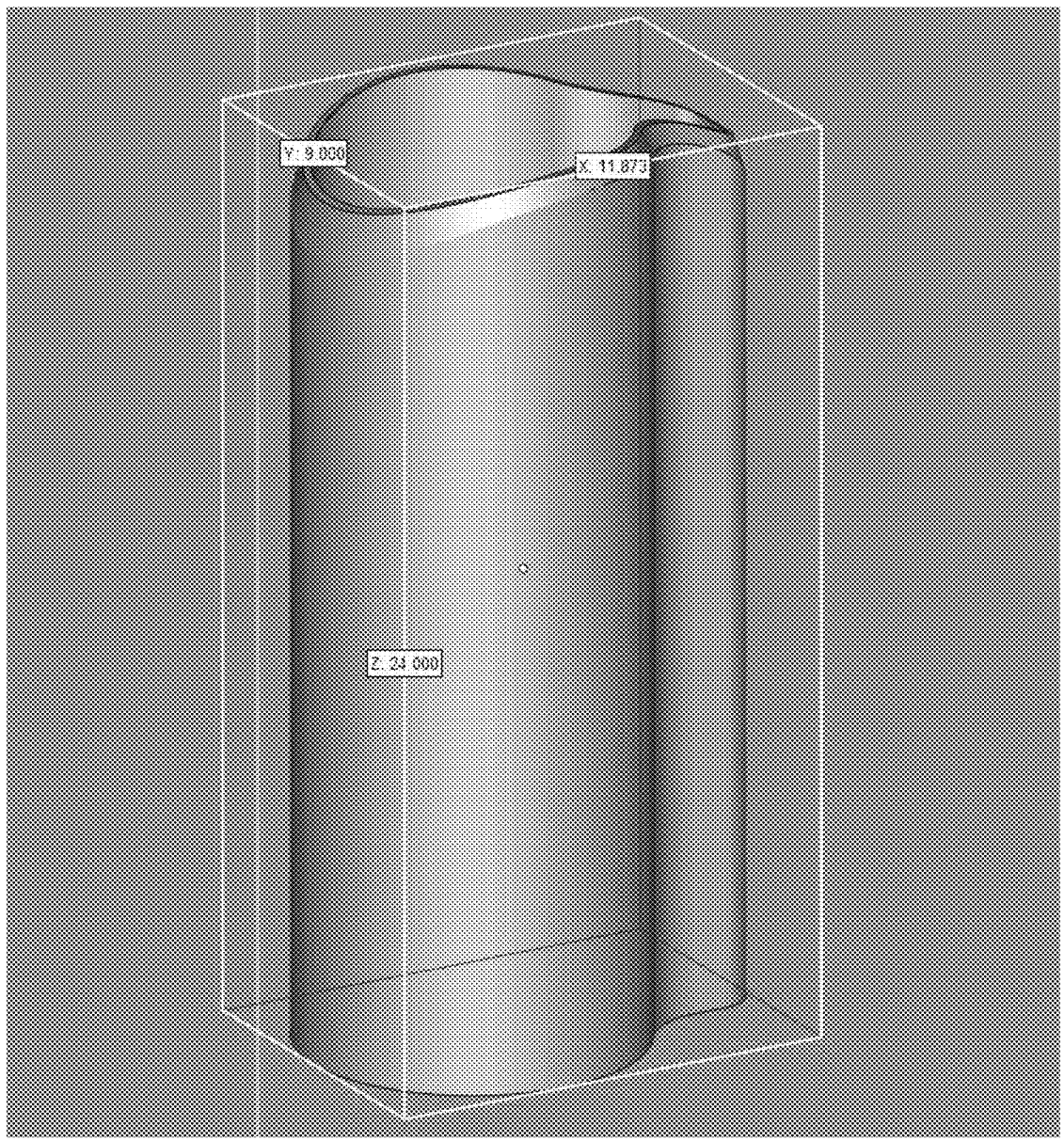
FIG. 5 is a top angle view of the cutting surface of the trephine.
Figure 6:
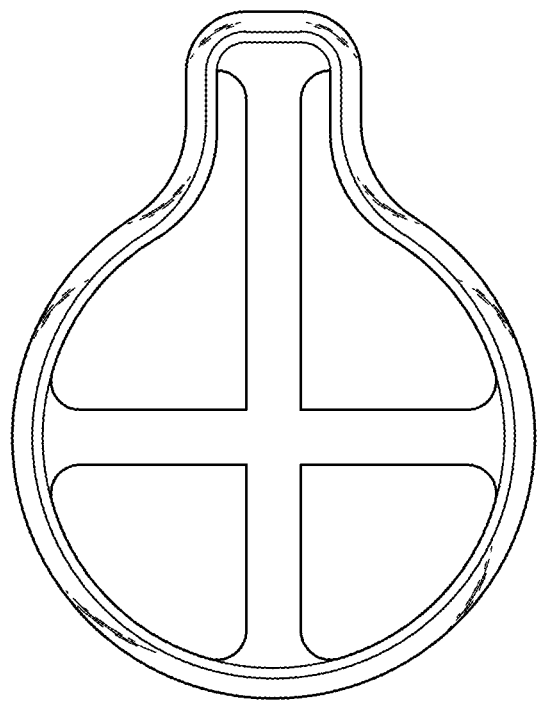
FIG. 6 is a cross-sectional view of the trephine including dimensions.

FIGS. 4, 5 and 6 show example illustrations of the keyhole shaped trephine used to cut the corneal implant from the donor cornea. The cutting procedure is performed in a sterile manner. Example dimensions are shown in FIG. 6. The keyhole implant shape is best illustrated in FIG. 6 showing a cross-sectional view through the trephine. The internal diameter of the disc section is 8 mm and the tail section has a width of 2 mm. The overall outer dimension for the disc region of the trephine is 9 mm and overall dimension including the disc and tail is 11.873 mm. The trephine has a cross-bar portion to maintain configuration of the trephine along its length. The cross-bar portion does not extend to the outermost portion of the trephine in order not to interfere with the corneal implant during cutting.

FIG. 5 shows a top perspective view across the cutting region of the trephine. As illustrated in FIG. 5 the cutting portion is rounded. The cutting surface is rounded in order to match the curvature of the posterior surface of the cornea. The curvature of the cutting edge would be approximately 7 mm to match the curvature of a normal cornea. This would be curvature of the punch block and would be mirrored in the trephine.

In embodiments the trephine is formed from cobalt chrome, which is used in hip prosthesis. Alternatively another biocompatible metal would be used to make the trephine. The trephine is not inserted inside the patient.

Figure 7:
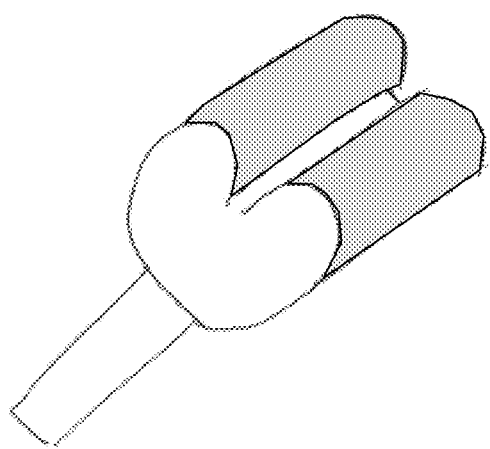
FIG. 7 shows a corneal implant.

The method for conducting the corneal transplant is now discussed with reference to FIG. 7, FIG. 8 and FIG. 9. The corneal implant tends to roll up into a scroll configuration after the endothelia cells have been removed from the stroma due to the very thin nature of the tissue (5 to 15 microns) as shown in FIG. 7. Preferably the figure is arranged such that the endothelial cells are on the outside of the scrolled implant naturally.

In preferred embodiments an ink stain is added to the implant, for example on the tail, on either the top or bottom surface to enable the surgeon to identify orientation of the implant and identify which surface includes the endothelial cells.

In further embodiments, convex or concave indentations are used as orientation marks on the graft. In further embodiments additional tails can be used to orient the graft prior to injection. The use of convex or concave indentations may be used as an alternative to ink stains or in addition to ink stains.

The use of indentations is a permanent solution which would be non-toxic. Convex indentations may be stronger and prevent the graft from tearing while concave indentations would not catch on any edges.

Further embodiments use further orientation features.

In event the tail breaks then the orientation marks can still be used to orient the graft and continue the surgery using conventional techniques.

In order to conduct the surgery the patient's cornea is prepared by making an incision 800 in the patient's eye. The incision is made in the cornea. The posterior region of the cornea is prepared by removing the damaged endothelial cells in the region required for endothelial transplant. This procedure is called a descementorhexis. The area of the cornea from which the diseased Descemet endothelial complex has to be removed is marked on the cornea. Multiple small incisions are made less than 1 mm in width are made at the cornea scleral limbus. The anterior chamber can be filled with air which is the preferred method or balanced salt solution. A reverse Synsky hook is inserted through the small incisions which prevents air or fluid escape and the edge of the endothelial disc to be removed is marked. The disc is scraped and mobilized toward the main incision (80-0). The endothelial cells are removed from the eye using a blade inserted through incision 800.

Cornea implant is inserted through incision 800 into the anterior chamber with the aim of occupying the denuded space. The corneal implant is centered and unrolled with the endothelial tissue of the corneal implant facing the posterior surface of the cornea in order to adhere to the patient's cornea.

Figure 8:
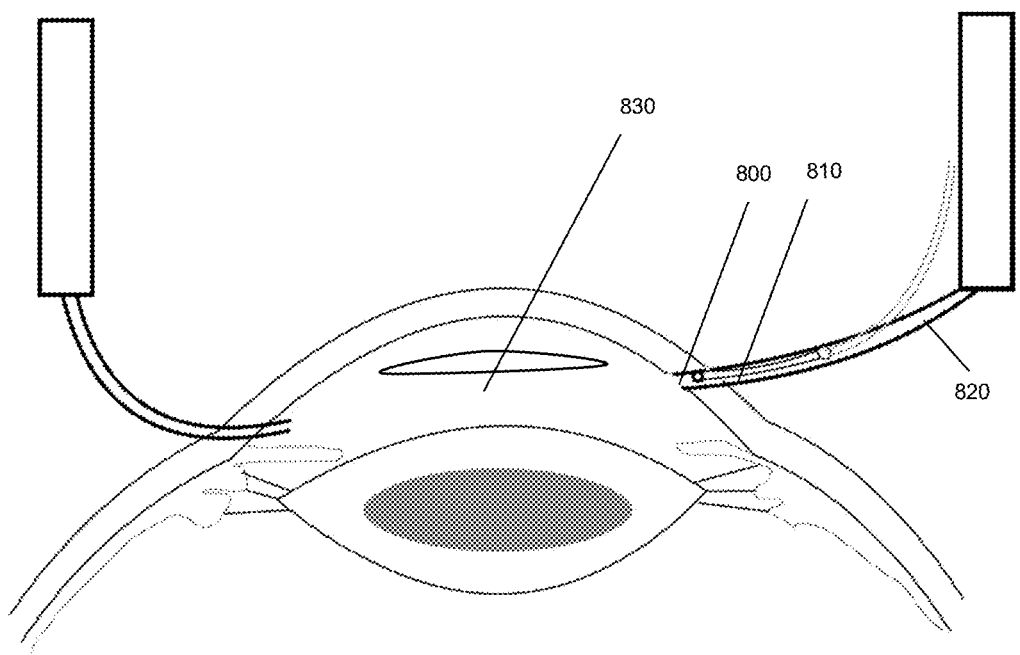
FIG. 8 shows insertion of the corneal implant into an anterior chamber of the eye.
Figure 9:
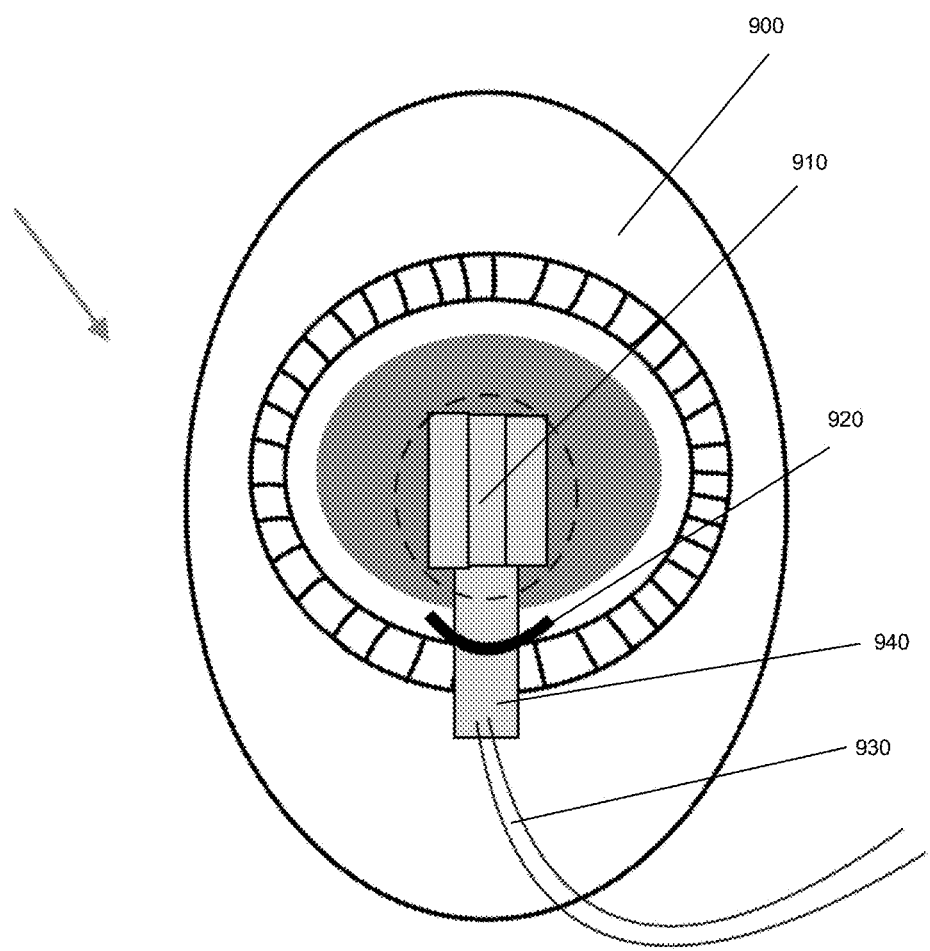
FIG. 9 shows a corneal implant positioned within the eye.

The embodiment of FIG. 8 shows corneal implant 810 loaded within delivery device 820 which may be in the form of a syringe or cartridge. The syringe or cartridge also includes fluid around the corneal implant to prevent it being damaged by the delivery device. In the example of FIG. 8 a suture is placed in the tail of the corneal implant in order to be able to accurately control the movement of the corneal implant within the syringe and from the syringe into the interior chamber of the patient's eye 830.

In the embodiment of FIG. 8 a further incision is made in the cornea at the opposite side of the eye from the first incision in order to manage the flow of fluid from the eye. In a further embodiment the incisions used for the descementorhexis can be used for the same purpose. This management of fluid through the eye assists in controlling the positioning of the corneal implant. The delivery system is connected to an irrigation line of a phaco emulsification machine. The system is set to a slow aspiration rate and low bottle height i.e. continuous irrigation. The corneal implant is delivered slowly releasing the suture. The corneal implant is arranged such that the tail portion remains behind within the syringe. In an alternative embodiment the corneal implant is delivered using the fluid in a syringe without continuous irrigation described above.

The tail portion of the corneal implant is used as the manipulating portion to which the suture may be attached. A benefit of using the tail portion as the manipulating region is that, since no contact is required to be made to the endothelial cells in the disc region, these cells are not damaged. Additionally, the sclera portion of the corneal implant tends to have greater integrity and is easier to manipulate than the endothelial portion.

The corneal implant is delivered into the interior chamber and the disc portion is centered into position for adhering to the posterior surface of the cornea. FIG. 9 shows a top view of an eye after the corneal implant 910 has been inserted into the interior chamber of the eye through incision 920. As illustrated in FIG. 9 after insertion corneal implant remains in the scrolled configuration. FIG. 9 also shows suture attached to tail 940 of the corneal implant. The incision 930 could also be closed with a suture to prevent accidental egress of the corneal implant out of the graft.

By manipulating the corneal implant in this controlled manner the orientation can be ensured by keeping the tail orientated correctly. The tail can be manipulated to center the corneal implant. If the tail inadvertently enters the eye, the suture may be used to draw the tail out. Unrolling the scrolled corneal implant may be achieved by moving an air bubble above the corneal implant although this may not be necessary when the width of the tail is significant in size compared with the disc portion. The use of air and tapping on the cornea is a well-established technique for unrolling the eye. Air is then injected deep into the corneal implant to aplanate it to the posterior surface of the recipient cornea. The air would be left in-situ for 30 mins. After the corneal implant has been inserted, positioned and unrolled, a stitch is inserted into the incision in order to seal the interior chamber of the eye. The tail portion of the corneal implant protrudes from the incision (see 940) and so can also be stitched and held in place. The stitching also retains the position of the corneal implant in order to aid with adhesion to the posterior surface of the cornea. In another embodiment of the procedure a stitch may be preplaced prior to injection of the graft so as not to disturb the wound once the graft is in place. This suture can be tightened after graft insertion and unrolling The protruding section of the tail may be cut or torn along the perforated section. In another embodiment a small needle can be inserted into the anterior chamber after graft adhesion and perforations can be created by the needle and the tail can then be removed. In another embodiment this could be performed post-operatively in the clinic after the graft adhesion is ensured. If the graft does not include perforations the tail can be cut or removed in another way.

In another embodiment the graft is loaded in an injector such that the tail emerges first. A forcep is introduced from the opposite side of the cornea through an incision into the anterior chamber to grasp and drag the graft by the tail. The tail is externalised delivering the graft into the anterior chamber with the tail outside. The incision is sutured. Various known techniques are used to unroll the graft. The tail is moved to manipulate the graft into unrolling and for centring the graft. The markings on the graft are used to reconfirm correct orientation. Once the graft is unrolled, air is injected deep to the graft to applanate the graft to the cornea.

It will be clear to those skilled in the art that embodiments of the present invention provide a corneal implant and method of surgery which enables a corneal implant to be inserted and manipulated within the anterior chamber of the eye and positioned to enable the transplant of endothelial tissue. The inclusion of a tail portion within the corneal implant provides a region of the implant which can be manipulated without fear of damaging important endothelial cells required for transplant. This helps increase the probability of conducting a successful surgery.

The specific embodiments described above are not limiting to the scope of the invention. In particular, the shape of the corneal implant is not limited to a keyhole configuration having a disc of endothelial tissue and a rectangular shaped tail including at least a portion of sclera. Instead, alternative shapes could be used which include a transplant portion including endothelial cells and a manipulating portion. The disc may be a semi-circle or cresenteric or annulus or star shaped to prevent the graft from rolling or to apply the graft to only those areas that need the tissue. The tail may be rectangular or triangular with a narrow portion near the disc or away from the disc. Alternatively any suitable shaped implant may be used.

Further embodiments of the corneal implant may have more than one tail or other notches or convex protrusions for manipulation, assistance with unrolling and for orientation.

Other shapes of the corneal implant may be used.

The shape of the transplant may be achieved by cutting with a blade or laser or printed on a scaffold to achieve a configuration mentioned above.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

What is claimed is:

1. A corneal implant comprising:
an implant portion comprising corneal endothelial tissue; and
a tail portion being usable to manipulate the corneal implant, connected to the implant portion, and comprising scleral tissue, a portion of the tail portion being configured to be removable from the corneal implant, the tail portion further comprising endothelial tissue; wherein the corneal implant further comprises a section having perforations, the section having perforations being positioned at a junction of the endothelial tissue of the tail portion and the scleral tissue of the tail portion.

2. A corneal implant according to claim 1, wherein the implant portion comprising corneal endothelial tissue is disk shaped.

3. A corneal implant according to claim 1 wherein the scleral tissue of the tail portion extends from an edge of the endothelial tissue of the tail portion.

4. A corneal implant according to claim 1 wherein the section having perforations is within the scleral tissue of the tail portion.

5. A corneal implant according to claim 1, the corneal implant being shaped such that on insertion into the anterior chamber of an eye the corneal implant adheres to the posterior surface of the cornea.

6. A corneal implant according to claim 1 wherein the implant portion further comprises corneal endothelium and Descement membrane.

7. A method for preparation of a corneal implant comprising: harvesting a corneal implant from the posterior surface of a cornea, the corneal implant comprising an implant portion comprising corneal endothelial tissue and a tail portion being usable to manipulate the corneal implant, connected to the implant portion, and comprising scleral tissue; a portion of the tail portion being configured to be removable; wherein the step of harvesting further comprises applying a trephine to the posterior surface of the cornea to harvest the corneal implant, the trephination being decentered on the posterior surface of the cornea.

8. A method for performing a corneal transplantation comprising the steps of:
  inserting at least part of a corneal implant into an anterior chamber of an eye, the corneal implant including an implant portion comprising corneal endothelial tissue, and a tail portion being usable to manipulate the corneal implant, connected to the implant portion, and comprising scleral tissue, a portion of the tail portion being configured to be removable from the corneal implant; and
  positioning the implant portion of the corneal implant to adhere to a posterior surface of the cornea.

9. A kit comprising the corneal implant of claim 1 and a fluid.

10. A kit according to claim 9 further comprising a delivery device for inserting the corneal implant into the anterior portion of an eye.

11. A corneal implant according to claim 1, wherein the corneal implant is keyhole shaped.

12. A method according to claim 7, wherein the trephine is keyhole shaped.

13. A corneal implant according to claim 1, wherein the tail portion is a projection that extends from an edge of the implant portion comprising endothelial tissue.

14. A corneal implant according to claim 1, wherein the section having perforations facilitates removal of the tail portion.

15. A corneal implant according to claim 1 wherein the implant portion comprising corneal endothelial tissue is disk shaped, and wherein the section having perforations is positioned at a junction of the disk shaped implant portion and the tail portion.

* * * * *